United States Patent
Keener et al.

(10) Patent No.: US 6,910,386 B1
(45) Date of Patent: Jun. 28, 2005

(54) METHOD FOR TESTING FLOW CHARACTERISTICS OF SEALING MATERIALS

(75) Inventors: Steven G. Keener, Trabuco Canyon, CA (US); Norman R. Byrd, Villa Park, CA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 10/761,171

(22) Filed: Jan. 20, 2004

(51) Int. Cl.$^7$ ............................................. G01N 11/00
(52) U.S. Cl. ..................... 73/822; 73/54.01; 73/54.02; 73/150 R
(58) Field of Search .......................... 73/150 R, 822, 73/54.11, 54.12, 866, 53.01, 64.41, 64.42, 73/64.43, 824, 845, 54.01, 54.02, 54.03, 73/433, 435, 32 R

(56) References Cited

U.S. PATENT DOCUMENTS

| | | | |
|---|---|---|---|
| 2,660,051 A | * | 11/1953 | Dowling ........................ 374/51 |
| 4,487,069 A | * | 12/1984 | Ishikawa et al. ............. 73/606 |
| 5,253,535 A | | 10/1993 | McCown |
| 5,517,860 A | | 5/1996 | Lin et al. |
| 6,435,034 B1 | * | 8/2002 | Schlapfer et al. ............. 73/768 |
| 6,520,004 B1 | | 2/2003 | Lin |
| 6,532,797 B1 | | 3/2003 | Hackett, Jr. |
| 2002/0043773 A1 | | 4/2002 | Philipson |

\* cited by examiner

*Primary Examiner*—Michael Cygan
(74) *Attorney, Agent, or Firm*—Alston & Bird LLP

(57) ABSTRACT

A test method for determining, quantifying, and qualifying the flow characteristics of a sealant material compound comprising the steps of applying a uniform layer of known initial mass of sealant material between two test surfaces and compressing the sealant material between the surfaces at a specific pressure for a specific length of time, and at a specific temperature, causing an amount of sealant to be extruded from between the test surfaces. The amount of the extruded sealant is measured and compared to the total mass of initial sealant material to determine the ratio of the extruded to initial sealant material. Based upon the mass ratio of extruded sealant material versus the initial sealant material, the flow characteristics of the sealant material may be expressed for any given combination of temperature, pressure, and duration and compared to other sealant materials.

16 Claims, 3 Drawing Sheets

METHOD FOR TESTING FLOW CHARACTERISTICS OF SEALING MATERIALS

FIELD OF THE INVENTION

The invention relates to a method of testing the properties and characteristics of sealant materials. More particularly, the invented method relates to a method of measuring and quantifying the flow characteristics of sealant materials.

BACKGROUND OF THE INVENTION

High-integrity, high-performance aerospace structures are often fabricated by overlaying sheets of metallic or non-metallic materials and fastening the sheets to one another with fasteners, such as rivets or bolts. A series of connected sheets may be fastened together to form complex structures such as aircraft fuselages and fuel tanks.

When the sheets of material are fastened together, the surfaces of the sheets are placed in intimate contact with one another and become, for all intents and purposes, invisible without any discernable boundary. These surfaces are known as "faying surfaces". The respective faying surfaces must intimately mate with one another in order to provide a strong physical connection or bond between the sheets of material. The conformance of the faying surfaces is even more important if the resultant fabricated structure is to contain volumes of liquid or gas. For instance, the faying surfaces of an aircraft fuselage must prevent the escape of air from a pressurized cabin, and the faying surfaces of an aircraft fuel tank must prevent the leakage of fuel.

Sealant materials are often applied to faying surfaces and to fasteners disposed through the faying surfaces to provide improved sealing and impermeability to liquids and gases contained within the fabricated and assembled structures. Fay-surface sealants are retained in a compressed state between the faying surfaces of the joined structural components and must not flow or squeeze out from between the mating fay-surfaces during the service life of the assembled article. Still, in these situations the composition must show sufficient compliance or flow characteristics to adequately effect a seal between the two mating fay surfaces, particularly if those surfaces possess slight irregularities or are otherwise not perfectly conforming.

Liquid or wet polysulfide resins are the most used faying-surface sealant materials because of their favorable chemical and physical properties, their ability to be pigmented, and their acceptance as an effective and efficient sealant system for use in the aircraft industry. However, since these sealant materials are applied in a wet, viscous state, the coated objects are difficult to handle after having the wet liquid polymer resins applied to them. Furthermore, the polysulfide sealant materials tend to degrade once in contact with high sulfur fuels typically used in aerospace applications.

Several alternatives to wet polysulfide sealant materials have been proposed over the years. Many of these alternatives use dry application processes and avoid the need for complicated wet applications. Nitrile-phenolic-based, thin-film adhesives provide for improved fuel tank sealing performance over the conventional wet, polysulfide sealing method. Also, sealant materials including fluoroelastomers, fluorosilicones, polyesters, polythioethers, polyurethanes, and polyureas have been developed. In addition, many technological advances in corrosion-inhibiting pigments, greatly reduced time and temperature curing parameters, elimination of fastener re-torquing requirements, and reduced environmental effects have been demonstrated with the new dry sealant material formulations. Furthermore, "dry" sealant materials have better abrasion resistance than the "wet" polysulfide materials; and, the lower density (approximately 1.1 gm/cm$^3$ versus approximately 1.34 gm/cm$^3$) results in a lower weight per unit area.

In the highly technical world of aerospace, there is an ever-present need for the significant and accurate prediction, quantification, and qualification of the various characteristics of materials such as sealants, in order to adequately compare the physical, chemical, and mechanical properties and characteristics of the sealants. For instance, although a variety of sealants are now available, there is no uniform basis available to compare the flow characteristics of one sealant material versus another. Standard measurements of viscosity do not adequately describe the flow of a cured polymer compressed between two faying surfaces. Further, standard measurements of elasticity do not adequately represent the characteristics of sealants under conditions of repeated compression and relaxation.

It is, therefore, desired to provide a method of testing sealant materials under standardized conditions that result in measurements and quantifications of the flow characteristics of these sealant materials. It is further desired to provide a method of testing the flow characteristics of these sealant materials that result in measured properties that enable the comparison of one material with another.

SUMMARY OF THE INVENTION

The invention is a test method that is specifically designed to measure and quantify the flow characteristics of sealant materials in order to objectively quantify those characteristics and, further, in order to provide a basis for comparison of one material to another. Material characteristics determined by this test method provide a better understanding and means for comparison between proposed, newly developed sealant materials and existing sealant materials, and provides a basis for predicting the performance of sealant materials that will eventually be introduced and used in mechanical joints, such as those common in airframe structures.

The invented test method comprises applying a substantially uniform layer of a known initial mass of sealant material between two test surfaces and compressing the sealant material between the surfaces at a specific pressure, for a specific length of time, and at a specific temperature. Compression of the sealant material causes the sealant material to flow, resulting in an amount of the sealant material being extruded from between the test surfaces. The amount of the extruded sealant material corresponds to the flow characteristics of the sealant material under the test conditions. The mass of the extruded sealant material may be measured and compared to the initial mass of the sealant material layer to determine the mass ratio of the sealant material that has been extruded. The flow characteristics of the sealant may be expressed for any given combination of temperature, pressure, and duration at said temperature and pressure based upon the mass ratio of the extruded sealant material versus the initial mass of sealant material.

The results of the test are dependent upon the surface area of the test surfaces. If the two test surfaces do not have the same surface area, the results of the test are dependent on the surface area of the smaller of the two test surfaces. For ease of comparison, it is advantageous to always test surfaces of equivalent surface area. Preferably, a standard test surface, such as 1-inch diameter circular test surfaces, is used for convenience in data reduction and standardized test results. However, as long as the surface area is recorded, results of tests with different surface areas can be proportionally adjusted for common area values.

Advantageously, the flow characteristics of a sealant material may be expressed as a flow value calculated as $$\text{Flow} = 100 \times B/A$$

where "A" is the initial mass of sealant material, and "B" is the mass of the material extruded from between the two test surfaces. This flow value is a characteristic of the tested sealant material.

The testing methodology delineated herein provides a new and proven approach for determining, quantifying, and evaluating the properties associated with newly developed materials, particularly aerospace sealing materials. Furthermore, it provides an approach for comparing the properties of various materials, such as the comparison of newly developed materials to those of existing materials.

The test method also provides for the prediction of how sealant materials will behave under actual use conditions. Prediction of sealant material properties requires a good understanding of material behavior under a wide variety of actual environmental and operating conditions, along with the associated failure mechanisms resulting from such conditions. By testing the flow characteristics of sealant materials under a variety of times, temperatures, and pressures similar to those experienced during actual use of the sealant material, the data obtained from such tests may be used to predict the behavior of the material under actual use.

Attributes of the sealant materials that may be compared and used to predict actual use behavior include long-term aging resistance, resistance to elevated temperature, and temperature cycling. Long-term aging resistance may be predicted by either testing specimens held at greatly extended periods of temperature and comparing them to specimens for similar lengths at room temperature, or by comparing shorter term test data at different elevated temperatures to prior, known long-term data from actual applications. To predict resistance to elevated temperature and temperature cycling, the sealant material may be maintained at elevated temperature, repeatedly heated and cooled, or cycled under pressure for a period of days or weeks in the laboratory. Such test cycles are equivalent to heat or pressure cycles that would occur over a period of months or years in actual use.

Prior to the invented testing methodology, no test method was available for the proper evaluation of the flow characteristics of new sealant materials under conditions that are typical of those real world conditions that cause flow of sealants during actual use. By evaluating the sealant materials under conditions that are controlled, but that emulate the actual, real world conditions of the applications, a more accurate measure and prediction of sealant material flow characteristics have been devised. The invented method is useful in comparing the characteristics of sealant materials in generally and is particularly useful in the comparison of fay-surface sealants.

BRIEF DESCRIPTION OF THE DRAWINGS

Figure 1:
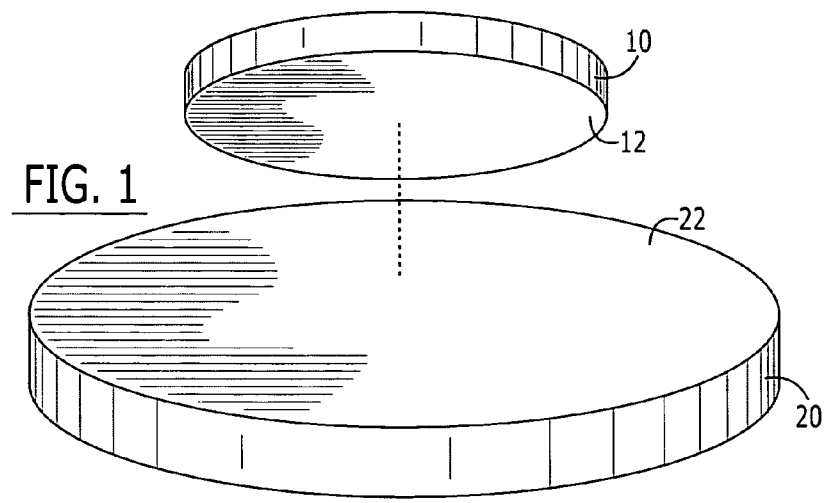
Figure 2:
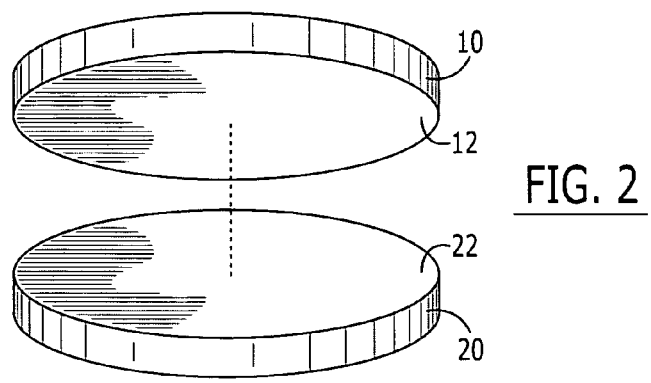
Figure 3:
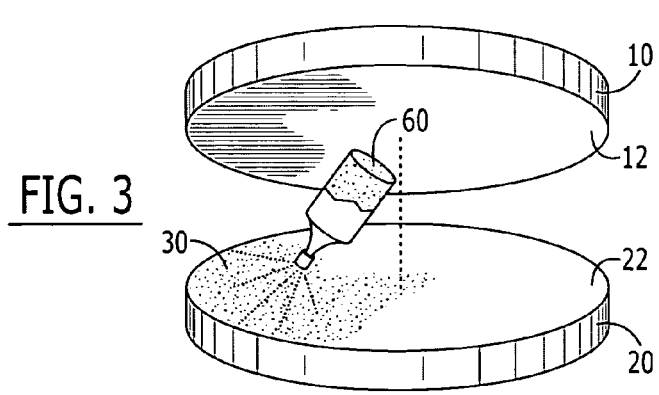
Figure 4:
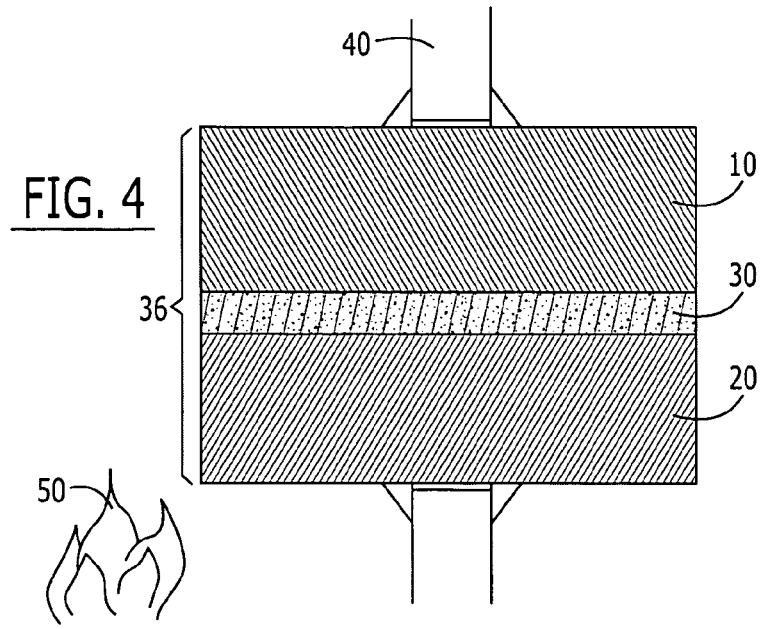
Figure 5:
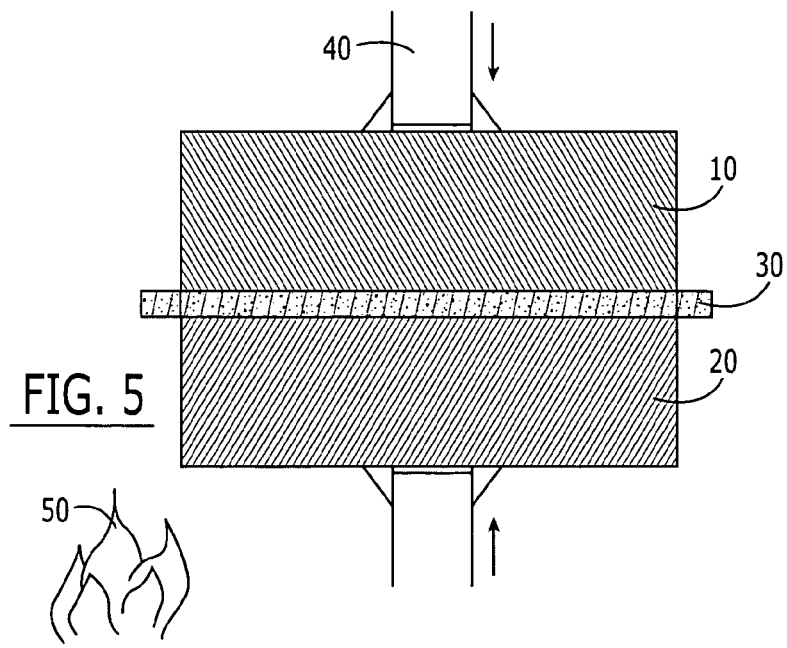
Figure 6:
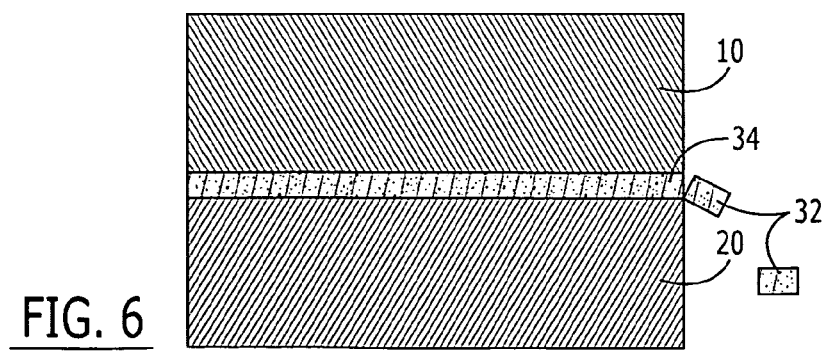
Figure 7:
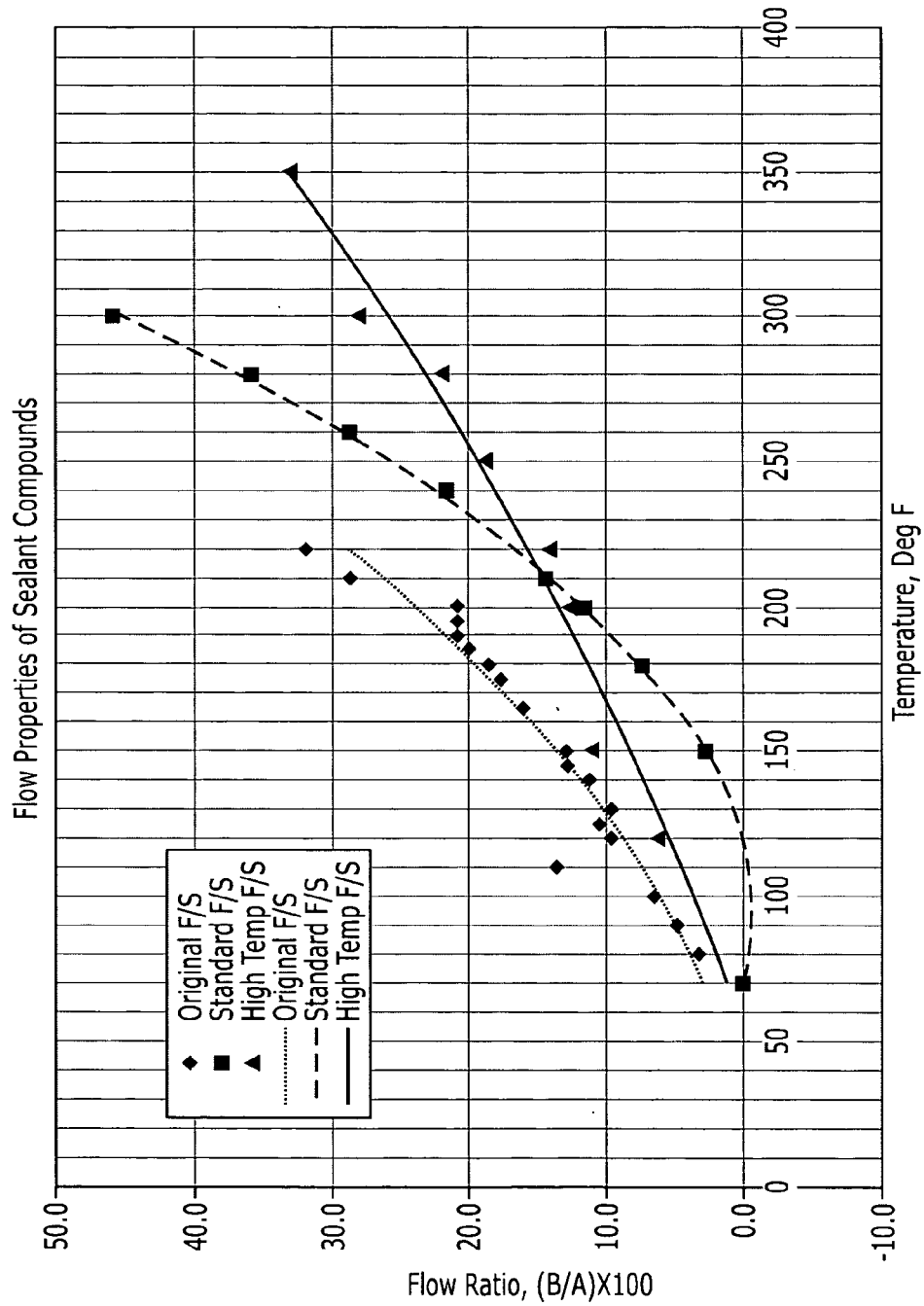

Having thus described the invention in general terms, reference will now be made to the accompanying drawings, which are not necessarily drawn to scale, and wherein:

FIG. 1 is a drawing showing test specimens in accordance with an embodiment of the invention;

FIG. 2 is a drawing showing test specimens in accordance with another embodiment of the invention in which the first and second test specimens have a common surface area;

FIG. 3 is a drawing depicting the application of a sealant material to the surface of a test specimen in accordance with an embodiment of the invention;

FIG. 4 is a drawing depicting the placement of a test assembly into a press under heat in accordance with an embodiment of the invention;

FIG. 5 is a drawing depicting the application of pressure to the test assembly under heat in accordance with an embodiment of the invention;

FIG. 6 is a drawing depicting the removal of extruded sealant material from the test assembly in accordance with an embodiment of the invention; and, FIG. 7 is a graph showing flow properties of exemplary sealant materials tested in accordance with an embodiment of the invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIG. 1, the sealant to be tested is applied between a lower test surface 12 of an upper test specimen 10 and an upper test surface 22 of a lower test specimen 20. Each of the test surfaces are advantageously flat, and the upper and lower surfaces are advantageously similarly shaped and advantageously have the same, known surface area. Preferably each specimen is formed of a material for which the sealant material is designed. For aerospace applications, the test surfaces are typically aluminum or an aluminum-alloy material but may also be non-metallic composite, polymer, or other material. Also, a standardized test specimen area, such as 1-inch diameter, is used in order to ease data reduction and standardized test results.

As used herein, the terms "upper" and "lower" are used to describe the test surfaces and test specimens of the invention in relationship to one another. The terms merely distinguish the respective surfaces and specimens and are not meant to limit the test method to any particular physical orientation with respect to an upward or downward position.

It has been found advantageous to use films, such as aluminum foil, as the test specimens. Such foils are inexpensive, easy to handle, and may be layered upon the platens of a laboratory press for easy compression.

If the mass of each test specimen is not already known, it is accurately determined and recorded prior to application of the sealant material so that the mass of the applied sealant material may be later determined.

If not already known, the surface area of the specimens between which the sealant material is to be applied is determined and recorded. If the surface area of one of the specimens is smaller than the other, as shown in FIG. 1, then the surface area of the smaller specimen is recorded since the smaller surface area will be the area from which the sealant material is extruded. According to an advantageous embodiment, shown in FIG. 2, the two specimens are of a uniform shape and surface area. Circular test specimens with 1-inch diameter surface areas are particularly advantageous due to ease of preparation and ease of comparison between samples, and standardization of test results.

Referring to FIG. 3, the sealant material 30 is applied to at least one of the test surfaces, for instance the lower test surface 22, by using the prescribed application method in the proper manner to achieve the thickness desired for testing of the sealant material. The test thickness of the applied sealant material should be equivalent to the thickness of the sealant material, as it will be actually used. A typical test thickness for the sealant material is from about 0.004 inch to about 0.05 inch, but the test material may be thinner or thicker than those that are typical. The sealant material is typically applied by spraying in accordance with instructions from the sealant supplier, or the sealant may also be applied using other methods, such as brushing or dipping. The sealant material is applied such that the thickness of the sealant material layer is substantially uniform across the surface area 22 of the coated test specimen 20. If both surface areas 12, 22 of the test specimens 10, 20 are coated, then the thickness of the coating material layer on surface area 12 is substantially uniform and the thickness of the coating material layer on surface area 22 is substantially uniform.

The application process and subsequent drying and curing time of a sealant material are related to the type of sealant material used. With a "wet" polysulfide sealant, a thixotropic mixture of an organic dichloride and sodium polysulfide is dispersed in an ionizing solvent to allow for the removal of the chlorine atom by the sodium ion (in the presences of a catalyst, such as lead oxide or manganese dioxide, which results in some degree of toxicity). The application of this type of sealant material is either by troweling or brushing on by either ejection from a roller nozzle or other applicator, and it remains soft for a considerable period of time. After application, the sealant material is allowed to adequately dry and fully cure. If allowed to occur at room temperature for wet sealant, this reaction is slow, hence it remains in the "wet" state for a considerable period of time before the product is fully cured and the reaction is complete. Consequently, drying periods for polysulfide or other wet sealant materials, which are cured by allowing diluents, solvents, or other volatiles to escape, may take about a week for the entire process to occur.

With a "dry" sealant, such as the polyurethane/polyurea, the reaction is more rapid and occurs in a neat, i.e., solvent-free, system as soon as the reactants (glycol/amine) are mixed with the isocyanate. The dry sealant material is applied from a dual-supply or chambered applicator for each component to be mixed under a prescribed ratio at the point of ejection for the reaction to be started. Once applied and properly mixed, the dry sealant material is tack-free within minutes and is fully cured within hours. Typical dry sealants, which set-up by curing with a catalyst, take approximately 15 to 20 minutes to dry and normally achieve full cure and cross linking of the polymer over night at either ambient room or slightly elevated temperature levels. Following application and proper cure, whichever sealant material type is used, the thickness of the material layer is measured to be certain it is within the desired material thickness range.

Referring to FIG. 4, once the sealant material has cured, the upper test surface 12 is positioned in contact with the exposed surface of the sealant 30 and aligned with the lower test surface 22 to form a sandwich structure comprising the upper specimen 10, sealant 30, and lower specimen 20. The sandwich structure is referred to as the test specimen assembly. The test specimen assembly is precisely weighed and the weight is recorded.

If the specimens are of different areas, the sandwich structure is formed such that no part of the smaller specimen extends beyond the surface area of the larger specimen. See FIG. 1, where specimen 10 has a smaller surface area 12 than the surface area 22 of specimen 20. Referring back to FIG. 2, the specimens are advantageously the same shape and size and are arranged such that the upper surface 12, sealant 30, and lower surface 22 share a common periphery 36. By common periphery, it is meant that the edges of the upper surface 12, lower surface 22, and sealant material layer 30 are aligned at all positions of the sandwich structure.

After weighing, the test specimen assembly is placed in a test machine 40, such as an Instron™ heated press or similar test equipment, and heated to a specific test temperature. Heat may be supplied to the assembly by heated platens of the laboratory test equipment or by another type of external heat source 50. The test temperature should approximate the operating temperature that the sealant material will experience during actual use, and typically, the test will be repeated at various temperature levels between about +100° F. and about +500° F., for example, +150° F., +180° F., +200° F., and +250° F. For each test temperature, the test specimen assembly is allowed to stabilize at the test temperature.

Referring to FIG. 5, once the temperature of the test specimen assembly is stabilized, a load is applied by the test equipment 40, so that a specific, known pressure is applied to the sealant material in a direction normal to the layer of sealant material. The specific pressure can be between about 50 psi and about 250 psi, for instance, 100 psi, and is maintained for a specific duration of time. This duration of time can be from about 30 seconds to several hours, but preferably about 5 minutes. While under pressure, the sealant material layer 30 exhibits a tendency to flow from between the test specimen surfaces. As used herein, the terms "flow" and "extrude" are used interchangeably to describe the movement of at least a portion of the sealant material layer 30 from between the surface areas 12, 22 of the test specimens 10, 20 under test conditions. The amount of sealant material that flows from between the surfaces corresponds to the flow characteristics of the sealant material under the testing parameters, i.e., time, pressure, and temperature conditions.

Referring to FIG. 6, after the specific test time duration has elapsed, the pressure is released from the test specimen assembly and the assembly is allowed to cool to ambient room temperature. Once at ambient room temperature, those portions of sealant material 32 that have been extruded are carefully trimmed from the test assembly. After trimming, each test specimen assembly is again precisely weighed and the mass of each test specimen assembly is recorded.

The flow characteristics of the sealant material, as measured in accordance with the invented test method, are expressed as a numerical value determined from the mass of extruded sealant material relative to the initial mass of sealant material. This ratio or flow value represents the flow characteristics of the sealant material as measured under the specific temperature, pressure, and time conditions of the test.

According to one embodiment of the invention, the flow characteristics of a sealant material are expressed by first determining the initial mass of sealant material in the test specimen assembly as the weight of the test specimen assembly before testing, minus the combined weight of the two test specimens. This value is termed "A". Secondly, the weight of the trimmed sealant material is calculated by subtracting the weight of the test specimen assembly after trimming from the initial weight of the test specimen assembly before testing. The result is termed "B". Finally, the percentage of extruded material is expressed as the flow value of the sealant material, calculated as $$Flow = 100 \times B/A$$

The flow characteristics of each sealant material is reported as a number that is further identified by the temperature at which the sealant material was tested, the pressure under which the sealant material was compressed, and the length of time that the sealant material was held under that temperature and pressure. The test method is preferably performed at multiple times, temperatures, and pressures. The results for each sealant material are charted or plotted to show the flow properties for the tested sealant material.

For comparison, two sealant materials may be subjected to the invented test method between test specimens of similar surface area, at equivalent temperatures, pressures, and lengths of time, or in a common range of temperatures, pressures, and times. FIG. 7 is an exemplary graph showing the comparison of three sealant materials tested in accordance with the invention over a range of temperatures but at common test pressures and utilizing standardized 1-inch diameter test specimens. The results of the tests for each sealant material may be easily compared with reference to the respective resulting flow properties at specific conditions or charted over a range of conditions. Thus, the invented test method provides a standardized, uniform procedure for measuring, quantifying, qualifying, and comparing the flow characteristics of new and existing sealant materials, and a reliable method for comparing the flow characteristics of one sealant material to another.

EXAMPLE

Cole Parmer® #-H01017-50 disposable aluminum weighing dishes were chosen as lower test specimens for testing a sealant material. A GX-8™ spray gun and FF3500 proportioner unit, both available from Gusmer Corporation, Lakewood, N.J., were used to apply Hi-Kote F/S™ sealant material, available from Hi-Shear Corp., Torrance, Calif. to the upper surface of the lower test specimen at a uniform thickness of 0.004 inch. The sealant was allowed to dry for 15 minutes at room temperature.

The coating thickness was measured with a Gardco Posi-Fector®, Model No. DF-6001FN, handheld electronic nondestructive gauge, and the sealant material layer was found to be uniformly applied to the aluminum substrate to within 0.0005 inches of the target 0.004-inch thickness. The sealant was then allowed to cure for 24 hours at room temperature.

Once cured, the sealant was covered with a layer of aluminum foil to make a sandwich. Using a die capable of cutting reproducible 1-inch diameter circles from a "sandwich" assembly, four 1-inch diameter circular test specimen assemblies were cut from the sandwich. Each test assembly was weighed and the weight recorded using an analytical balance capable of weighing to within an accuracy of 0.1 milligrams.

After weighing, the first test assembly was placed in a press with heated platens capable of measuring and controlling temperatures to within 1° C. and pressure to within 10 psi. The press was heated to a temperature of +150° F.

The test assembly was allowed to stabilize at the test temperature for 10 minutes. Once stabilized, a load of 100 psi was applied for 5 minutes. The test assembly was then removed from the press and allowed to cool to room temperature, and any extruded material was trimmed from the circular test assembly by running the test assembly through the 1-inch circular die. After trimming, each test assembly was again weighed and the weight was recorded.

The method of heating, pressing, and determining the amount of extruded sealant material with respect to the first circular test assembly was repeated at +180° F., +200° F., and +250° F., for the second, third, and fourth circular dies, respectively.

The testing methodology delineated herein provides a new approach for evaluating and quantifying the material properties associated with newly developed materials, and, in particular, aerospace sealing materials. Prediction of material properties requires a good understanding of material behavior under a wide variety of real world environmental and operating conditions, along with the associated failure mechanisms resulting from these conditions. By testing the flow characteristics of sealant materials under a variety of temperatures and pressures, the data obtained from such tests may be directly compared to other materials at the same tested temperatures and pressures for purposes of quantifying and qualifying existing and new sealant material compounds.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for determining the flow characteristics of a sealant material, wherein the test method comprises:
   applying an initial mass of sealant material as a sealant material layer between a surface of a first test specimen and a surface of a second test specimen to form a test specimen assembly;
   providing pressure upon the test assembly so as to compress the sealant material between the first and second test specimens for a specific length of time, thereby extruding sealant material from between the two test specimen surfaces;
   determining the mass of sealant material extruded from the test specimen assembly after said length of time; and
   calculating a flow characteristic of the sealant material as the ratio of the mass of extruded sealant material to the initial mass of the sealant material layer.

2. The method of claim 1, wherein the step of applying the initial mass of sealant material as the sealant material layer comprises applying the sealant material as a uniformly thick layer.

3. The method of claim 2, wherein the step of applying a sealant material layer between a first and second test specimen surface comprises the steps of:
   applying an initial mass of sealant material as a uniformly-thick sealant material layer upon a first test specimen surface;

placing a second test specimen surface in contact with the exposed surface of the sealant material layer to form the test specimen assembly structure; and die-cutting the test assembly thereby providing the various layers of the test assembly with a common outer periphery.

4. The method of claim 2, wherein the first and second test specimen surfaces are metallic.

5. The method of claim 4, wherein the first and second test specimen surfaces are aluminum or aluminum-alloy foil surfaces.

6. The method of claim 2, wherein the first and second test specimen surfaces are non-metallic.

7. The method of claim 1, wherein the step of providing pressure to the test assembly comprises providing a known amount of pressure to the test specimens for a measured length of time.

8. The method of claim 7, wherein the temperature of the test surfaces is controlled and measured while pressure is provided.

9. The method of claim 1, wherein the steps of applying an initial mass of sealant material as the sealant material layer between the first and second test surfaces to form the test assembly;

providing pressure upon the test assembly;

determining the mass of sealant extruded from the common periphery after said length of time; and calculating the flow characteristic of the sealant as the ratio of the mass of extruded sealant to the beginning mass of the sealant;

are repeated at multiple test temperatures.

10. The method of claim 1, wherein the steps of applying an initial mass of sealant material as the sealant material layer between the first and second test surfaces to form the test assembly;

providing pressure upon the test assembly;

determining the mass of sealant extruded from the common periphery after said length of time; and calculating the flow characteristic of the sealant as the ratio of the mass of extruded sealant to the beginning mass of the sealant;

are repeated at multiple test pressures.

11. The method of claim 1, wherein the step of determining the mass of extruded sealant comprises trimming any sealant extruded from the test specimen assembly and weighing the trimmed sealant.

12. The method of claim 1, wherein the step of determining the mass of extruded sealant comprises measuring the beginning mass of the test specimen assembly prior to the application of pressure, trimming the extruded sealant after pressure has been applied, measuring the final mass of the test specimen assembly after the extruded sealant has been trimmed, and subtracting the beginning mass of the test specimen assembly from the mass of the test specimen assembly after trimming the extruded sealant material.

13. The method of claim 1, further comprising the step of expressing the flow value of the sealant as a numerical figure calculated as $$\text{Flow} = 100 \cdot (B/A)$$

where A=initial mass of sealant, and
B=mass of extruded sealant.

14. A method for determining the flow characteristics of a sealant for use between faying surfaces, wherein the test method comprises:

applying an initial amount of sealant material as a uniformly-thick layer between a first and second test surface to form a 1-inch diameter, circular sandwich structure aligned such that each of the layers of the sandwich have a common periphery;

placing the sandwich structure under compression of about 100 psi for about 5 minutes, thereby urging the sealant from between the two test surfaces;

determining the mass of sealant extruded from the common periphery after said length of time; and expressing the flow value of the sealant as a numerical figure calculated as $$\text{Flow} = 100 \cdot (B/A)$$

where A=initial mass of sealant, and
B=mass of extruded sealant.

15. A method of determining a flow characteristic profile for a sealant material, comprising the steps of subjecting several samples of the sealant material to the steps of claim 13 under uniform conditions but at different test temperatures for each sample; and, plotting the flow value of each sample versus the test temperature at which each respective flow value was obtained.

16. A method of determining a flow characteristic profile for a sealant material, comprising the steps of subjecting several samples of the sealant material to the steps of claim 13 under uniform conditions but at different test pressures for each sample; and, plotting the flow value of each sample versus the test pressure at which each respective flow value was obtained.

* * * * *